United States Patent [19]

Duran, Jr.

[11] Patent Number: 4,662,756

[45] Date of Patent: May 5, 1987

[54] MOTION TRACKING DEVICE

[75] Inventor: Michael J. Duran, Jr., Lancaster, Pa.

[73] Assignee: RCA Corporation, Princeton, N.J.

[21] Appl. No.: 611,997

[22] Filed: May 18, 1984

[51] Int. Cl.⁴ ........................................... G01N 21/86
[52] U.S. Cl. ..................................... 356/429; 250/561
[58] Field of Search ............................... 356/429–435, 356/372–375, 383–385; 250/548, 559, 560, 571, 561, 572, 562

[56] References Cited

U.S. PATENT DOCUMENTS

| | | | |
|---|---|---|---|
| 2,931,917 | 4/1960 | Beelitz | 250/560 X |
| 3,096,919 | 7/1963 | Snyder | 250/561 X |
| 3,456,118 | 7/1969 | Hartz | 250/559 X |
| 3,621,266 | 11/1971 | Akuta | 356/383 X |
| 3,746,451 | 7/1973 | Croissant et al. | 356/430 X |
| 3,761,723 | 9/1973 | De Cock | 356/383 X |
| 3,812,373 | 5/1974 | Hosoe et al. | 356/430 X |
| 3,835,332 | 9/1974 | Bridges | 356/430 X |
| 3,919,560 | 11/1975 | Nopper | 250/571 X |
| 4,261,013 | 4/1981 | Van Renseen et al. | 250/561 X |
| 4,303,189 | 12/1981 | Wiley | 226/15 |
| 4,511,803 | 4/1985 | Ross et al. | 356/431 X |
| 4,559,452 | 12/1985 | Igaki et al. | 250/561 X |

*Primary Examiner*—R. A. Rosenberger
*Attorney, Agent, or Firm*—E. M. Whitacre; D. H. Irlbeck; L. L. Hallacher

[57] ABSTRACT

A device for sensing the longitudinal edges of an aperture pattern in a longitudinally and transversely moving opaque strip of material includes a transversely moveable platform. Arrays of detector elements are supported on the platform and positioned such that some elements of each array are opposite the aperture patterns and other elements of each array are opposite the opaque borders of the strip. Energy sources are individually arranged on the side of the strip opposite the arrays whereby the elements opposite the aperture pattern receive energy and the elements opposite the borders are shielded. The energy conditions of the elements are detected and the platform is moved transversely to maintain an equal number of elements in both arrays opposite the apertures whereby the platform tracks the transverse motion of the strip.

7 Claims, 4 Drawing Figures

MOTION TRACKING DEVICE

BACKGROUND OF THE INVENTION

This invention relates generally to the tracking of the transverse motion of an aperture pattern in a longitudinally moving strip of material and particularly to the sensing of the longitudinal edges of the aperture pattern in the shadow mask web during the production of kinescope shadow masks.

In the manufacture of shadow masks for color television kinescopes a roll of flat material is coated with a photoresist material and is subsequently photoexposed to form a series of aperture patterns and the peripheries of the shadow masks in the photoresist material. The unexposed photoresist material is washed away leaving bare metal. The strip of material is subjected to an acid etching process in which the bare metal is removed to form the apertures and partially etched peripheries used to remove the shadow masks from the strip of material. After the etching is completed the transmission of energy through the apertures is measured to verify that the shadow masks are suitable for the intended use. The measurement of light transmission through the apertures typically is accomplished by shining a known intensity of light through the apertures and noting the percentage of light which passes through the apertures. The acid etching and the light transmission measurements typically are made while the strip of material is pulled longitudinally along a conveyor line. Because of the long length of the strip, there is a tendency for the strip to move transversely back and forth perpendicular to the longitudinal motion. The areas of the apertures varies along the transverse dimension of the pattern and for this reason, accuracy of the light transmission measurement requires that all measurements be made at the same transverse position of the aperture pattern. Accordingly, the transverse motion causes a degregation of the measurement accuracy. It is extremely difficult, if not impossible, to restrain the long strip and prevent the transverse motion. For this reason, there is a need for a system for tracking the transverse motion of the strip so that the measuring densitometer maintains a constant relative transverse position with respect to the strip. Accordingly, there is a need for a device for tracking the longitudinal edges of the aperture patterns as a technique of sensing the transverse motion. The instant invention fulfills this long felt need.

CROSS REFERENCE TO RELATED APPLICATIONS

This invention can be used as the sensor in the system described in Application Ser. No. 611,957 entitled "MOTION TRACKING SYSTEM AND METHOD" filed on even date herewith by Michael J. Duran, Jr.

SUMMARY

A device for sensing the longitudinal edges of an aperture pattern in a longitudinally and transversely moving opaque strip of material includes a moveable platform arranged substantially parallel to the plane of the strip of material. The platform is bilaterally moveable in a direction substantially parallel to the transverse motion of the strip. A device for measuring energy transmission through the aperture pattern is fixed to the platform. A first energy sensor having a plurality of individual energy responsive elements is supported by the platform between the platform and the strip of material. The sensor is positioned whereby some of the elements normally lie opposite one edge of the aperture pattern and the rest of the elements normally lie opposite an opaque border of the strip of material. A first energy source is supported by the platform and is positioned so that the strip of material passes between the energy source and the first sensor whereby the elements opposite the aperture pattern receive energy from the source and elements opposite the opaque border are shielded from energy from the source. A second energy sensor, which is similar to the first energy sensor, is in the proximity of the opposite edge of the aperture pattern. A second energy source is positioned so that the strip of material passes between the second energy source and the second energy sensor whereby elements of the second sensor opposite the other edge of the aperture pattern receive energy from the second energy source and elements opposite the other opaque border are shielded from energy from the second energy source. A means responsive to the elements of the energy sensors transversely moves the moveable platform with respect to the opaque strip whereby equal numbers of elements of the sensors receive energy from the energy sources as the strip moves transversely to maintain the relative positions of the aperture pattern and the measuring device.

DETAILED DESCRIPTION

Figure 1:
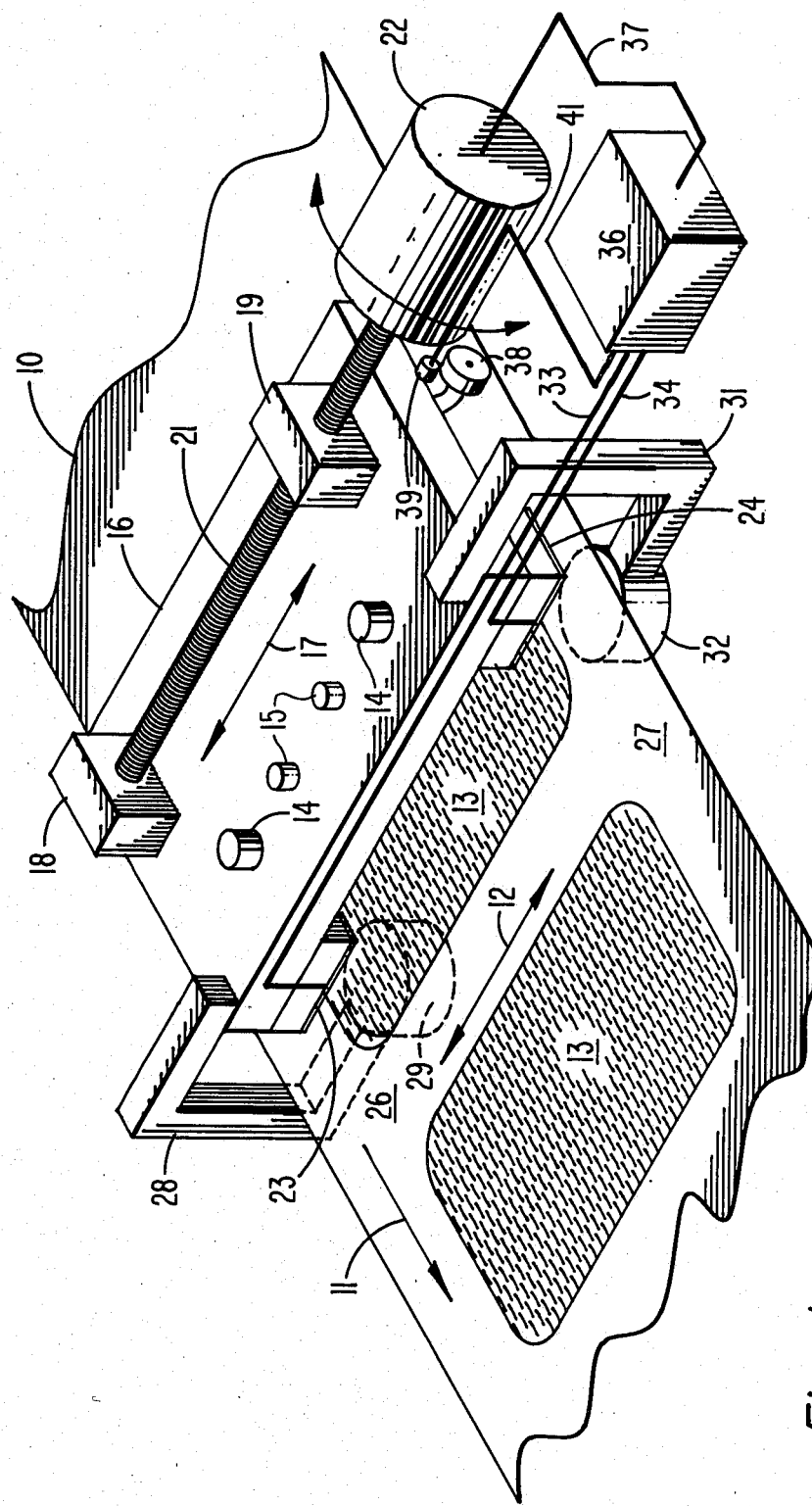
FIG. 1 is a perspective view of a preferred embodiment.

In FIG. 1, a strip of material 10 moves longitudinally in the direction indicated by the arrow 11. As is known to those skilled in the shadow mask art, the strip 10 is many feet in length and is pulled along by rollers (not shown). For this reason, the strip 10 also has a tendency to move transversely back and forth as indicated by the arrow 12. The strip 10 has been etched to form a succession of shadow masks each of which includes an aperture pattern 13 having a very large number of apertures. An important feature of a shadow mask is the ability to transmit electron beams through the apertures. The acceptability of the transmission capability typically is measured prior to removing the individual shadow masks from the strip 10 by measuring the light transmission capability of the aperture patterns. This typically is done using densitometers, such as 14, to measure the percentage of light which is passed through the apertures. The densitometers 14 can be of the type described in U.S. Pat. No. 4,289,406. In measuring the light transmission capabilities, the densitometers preferably are arranged opposite to particular transverse positions of the aperture pattern. Such positioning is used because the transverse aperture dimension varies along the transverse dimension of the shadow mask and, therefore, the areas of the apertures in the center of the shadow mask are different from that of those at the edges of the shadow mask. For this reason, the transverse motion indicated by the arrow 12 reduces the accuracy of the transmission measurements if the densitometers remain stationary.

A moveable platform 16 is arranged parallel to the surface of the strip 10. As indicated by the arrow 17, the platform 16 is moveable in a direction substantially perpendicular to the longitudinal axis of the strip 10 and accordingly parallel to the transverse motion of the strip 10 indicated by the arrow 12. Affixed to the platform 16 are two ball nuts 18 and 19 which are threaded to receive a lead screw 21. The lead screw 21 is driven by a motor 22. Accordingly, transverse motion of the platform 16 is affected by turning the motor 22 either clockwise or counterclockwise to effect the desired transverse motion of the platform.

Energy sensor arrays 23 and 24 are supported by the platform 16 between the platform and the shadow mask aperture patterns 13. Each of the arrays 23 and 24 contains a large number of individually energy responsive elements. In the preferred embodiment, the energy sensitive elements of the arrays 23 and 24 can be phototransistors commonly available in the art, for example, Model No. BPW-17N phototransistors available from AEG Telefuken can be utilized. The phototransistor array 23 is arranged so that some of the phototransistors lie opposite the aperture pattern 13 and other of the phototransistors are opposite the opaque border 26 of the strip 10. Similarly, the phototransistor array 24 is arranged so that some of the phototransistors are opposite the aperture pattern 13 and the other phototransistors are opposite the other opaque border 27. Accordingly, the longitudinal edges of the aperture pattern move between energy responsive elements in the two arrays. A bracket 28 is affixed to the platform 16 and supports a light source 26 on the side of the strip 10 opposite from the phototransistor array 23. Accordingly, the phototransistors which are opposite the aperture pattern 13 are illuminated by the light source 29. Similarly, a bracket 31 is affixed to the other side of the platform 16 and supports another light source 32 on the opposite side of the strip 10 and in the vicinity of the light source 24. Suitable conductors 33 and 34 couple the phototransistors of the arrays 23 and 24, respectively to a processing unit 36. The output line 37 of the processing unit 36 actuates the motor 22 to effect either clockwise or counterclockwise rotation of the lead screw 21 and transversely move the platform 16 in the desired direction.

Additional light sensors 15 are positioned on the platform 16. These sensors are illuminated through the aperture patterns 13 by additional light sources (not shown). These sensors sense the opaque areas between successive aperture patterns and inhibit the processing unit 36 when such areas are opposite the arrays 23 and 24.

A longitudinal motion sensor 38 is supported by the platform 16 to sense the longitudinal motion of the strip 10 so that no effort is made to move the platform 16 transversely when the strip 10 is not moving longitudinally. The longitudinal motion sensor 38 can be in the form of a nonconductive disc which contains one or more ferromagnetic slugs. A coil 39 is supported in the vicinity of the disk 38 and gives an output pulse each time a magnetic slug passes the coil 39. These pulses are fed to the processing unit 36 by a suitable conductor 41.

Figure 2A:
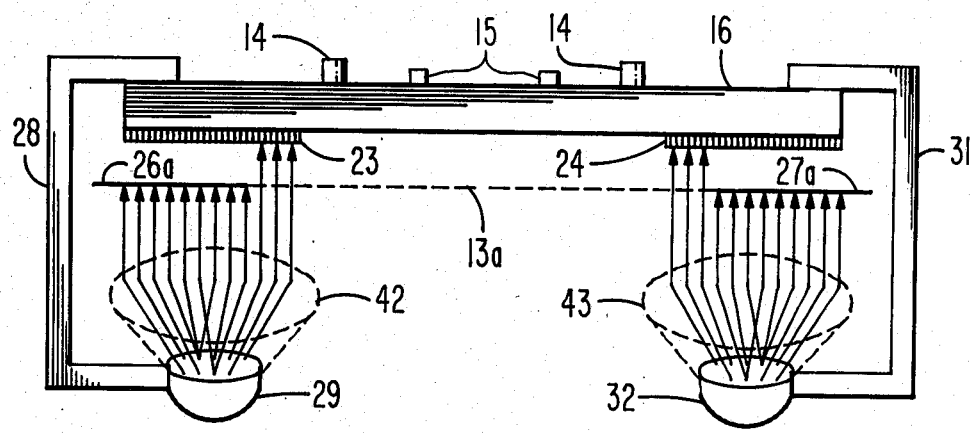
FIGS. 2a and 2b show how the preferred embodiment of FIG. 1 is useful with various sizes of shadow masks.
Figure 2B:
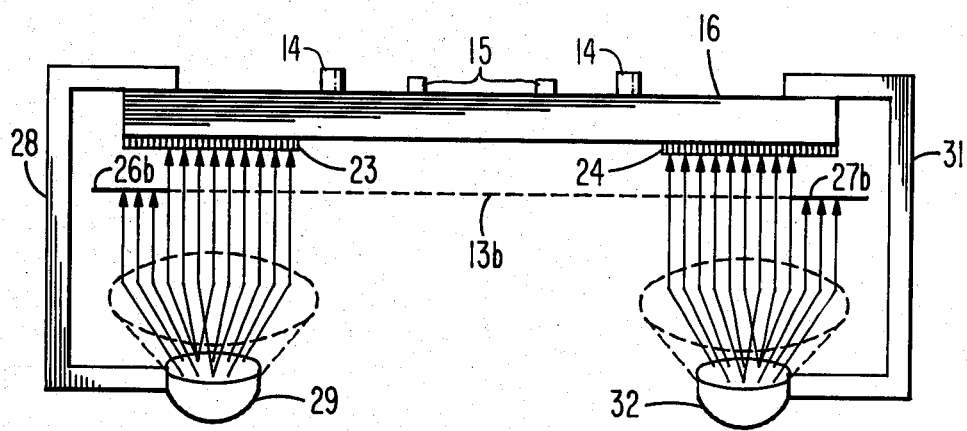

FIGS. 2a and 2b show how the device can be used in conjunction with aperture patterns of various sizes. In FIG. 2a, the light source 29 includes a lens 42 and the light source 32 includes a lens 43. The output of the light sources are focused by the lenses so that the light rays are substantially parallel. The aperture pattern 13a is of a size such that a small number of phototransistors in each of the arrays 23 and 24 are illuminated by the light rays passing through the aperture pattern 13a while most of the phototransistors are shielded by the opaque borders 26a and 27a. In FIG. 2b, the aperture pattern 13b is larger than the pattern 13a of FIG. 2a. Accordingly, more of the light from the sources 29 and 32 passes through the aperture pattern and impinge upon the phototransistors within the arrays 23 and 24 while only a few rays are blocked by the opaque borders 26b and 27b. Thus, a wide variety of aperture pattern sizes can be used with the inventive device. The aperture pattern 13a can be a 13V kinescope shadow mask (13 inch, 3 cm diagonal) and the aperture pattern 13b can be a 25V kinescope shadow mask (25 inch 63.5 cm diagonal).

Figure 2C:
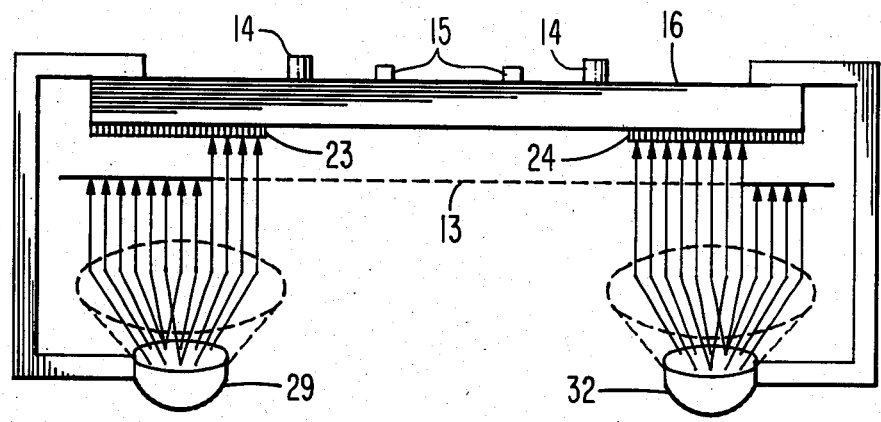
FIG. 2c shows how the transverse motion of the strip of material is sensed.

In FIGS. 2a and 2b, equal numbers of phototransistors in the arrays 23 and 24 receive energy from the light sources 29 and 32 indicating that the platform 16 is in the desired centered position over the strip 10. In FIG. 2c more phototransistors in the array 24 receive light than phototransistors in the array 23, indicating that the strip 10 has drifted transversely to the right. The energy state of each of the phototransistors within the two arrays 23 and 24 are provided to the processing unit 36 which then energizes the motor 22 to transversely move the platform 16 to the left until an equal number of phototransistors in both of the arrays 23 and 24 receive light from the respective light sources. Thus, the inventive device tracks the transverse motion of the strip 10 rather than making an effort to restrain the strip from such transverse motion.

What is claimed is:

1. A device for sensing the longitudinal edges of an aperture pattern in a longitudinally and transversely moving opaque strip of material comprising:
    a moveable platform arranged substantially parallel to the plane of said strip of material, said platform being longitudinally fixed and bilaterally moveable in a direction substantially parallel to the transverse motion of said strip of material;
    means for measuring energy transmission through said aperture pattern, said means for measuring being fixed to said platform to measure energy transmission through a particular transverse position of said aperture pattern;
    a first energy sensor having a plurality of individual energy responsive elements fixedly supported by said platform between said platform and said strip of material, said sensor being positioned whereby some of said elements normally lie opposite one longitudinal edge of said aperture pattern and the rest of said elements normally lie opposite an opaque border of said strip of material;
    a first energy source fixedly supported by said platform positioned so that said strip of material passes between said energy source and said first sensor whereby said elements opposite said aperture pattern receive energy from said source and elements opposite said opaque border are shielded from energy from said source;
    a second energy sensor, similar to said first energy sensor, fixedly supported by said platform and positioned in the proximity of the other longitudinal edge of said aperture pattern, a second energy source fixedly supported by said platform positioned so that said strip of material passes between said second energy source and said second energy sensor whereby elements of said second sensor opposite said other edge of said aperture pattern receive energy from said second energy source and elements opposite the other opaque border are shielded from energy from said second energy source;

means responsive to said elements of said first and second energy sensors for transversely moving said moveable platform with respect to said opaque strip whereby equal numbers of elements of said first and second sensors received energy from said first and second energy sources as said strip moves transversely to maintain the relative transverse positions of said aperture pattern and said means for means; and means for sensing longitudinal motion of said strip of material to inhibit transverse motion of said strip of material in the absence of said longitudinal motion.

2. The device of claim 1 wherein said first and second sensors are phototransistor arrays and said first and second energy sources are light sources.

3. The device of claim 1 wherein said means responsive to said sensors includes a motor and a lead screw.

4. The device of claim 3 wherein said means for measuring energy transmission through said aperture pattern includes at least one densitometer for measuring light transmission.

5. The device of claim 1 further including means for sensing the opaque areas between successive aperture patterns.

6. A method of sensing the longitudinal edges of an aperture pattern in a transversely and longitudinally moving strip of material comprising the steps of:

arranging a transversely moveable and longitudinally fixed platform substantially parallel to the plane of said strip and substantially perpendicular to the longitudinal axis of said strip;

fixedly arranging arrays of energy sensitive elements on said platform and in the proximity of the longitudinal edges of said aperture pattern such that when said strip is centered equal numbers of elements in each array are opposite said aperture patterns and equal numbers of elements in each array are opposite the opaque borders of strip;

fixedly arranging energy sources on said platform in positions to individually provide energy to the elements of said arrays whereby the elements opposite said aperture pattern receive energy and the elements opposite said opaque borders are shielded from energy;

detecting the energy conditions of the elements of the arrays as said strip moves longitudinally and transversely and transversely moving said platform in the direction of transverse motion of said strip to maintain the same number of elements in each of said arrays opposite said aperture pattern whereby the relative transverse positions of said aperture pattern and said device for measuring are maintained; and sensing the longitudinal motion of said strip and inhibiting transverse motion of said platform in the absence of said longitudinal motion.

7. The method of claim 6 wherein said energy sensitive elements are phototransistors and said energy sources emit light.

* * * * *